(12) United States Patent
Musuvathi et al.

(10) Patent No.: US 9,384,239 B2
(45) Date of Patent: Jul. 5, 2016

(54) PARALLEL LOCAL SEQUENCE ALIGNMENT

(71) Applicant: Microsoft Corporation, Redmond, WA (US)

(72) Inventors: Madanlal Musuvathi, Redmond, WA (US); Todd Mytkowicz, Seattle, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 521 days.

(21) Appl. No.: 13/716,231

(22) Filed: Dec. 17, 2012

(65) Prior Publication Data
US 2014/0172824 A1    Jun. 19, 2014

(51) Int. Cl.
*G06F 17/30*      (2006.01)
*G06F 19/22*      (2011.01)

(52) U.S. Cl.
CPC .......... G06F 17/30445 (2013.01); G06F 19/22 (2013.01)

(58) Field of Classification Search
CPC ....................................................... G06F 19/22
USPC .................................................. 707/705, 706
See application file for complete search history.

(56) References Cited

U.S. PATENT DOCUMENTS

| | | | |
|---|---|---|---|
| 7,917,299 B2 | 3/2011 | Buhler et al. | |
| 8,116,988 B2 | 2/2012 | Glick et al. | |
| 8,572,407 B1 * | 10/2013 | Chengottarasappan et al. | 713/190 |
| 2002/0048763 A1 * | 4/2002 | Penn et al. | 435/6 |
| 2002/0081590 A1 * | 6/2002 | Penn et al. | 435/6 |
| 2003/0187587 A1 * | 10/2003 | Swindells et al. | 702/19 |
| 2003/0194704 A1 * | 10/2003 | Penn et al. | 435/6 |
| 2009/0205085 A1 * | 8/2009 | Goldman et al. | 800/298 |
| 2012/0239706 A1 | 9/2012 | Steinfadt | |

OTHER PUBLICATIONS

Rognes et al. (Six-fold of Smith-Waterman sequence database searches suing parallel processing on common microprocessors), pp. 699-706, 2000.*
Li et al. (Fast and accurate long-read alignment with Burrows-Wheeler tranform), vol. 26, No. 5 2010, pp. 589-595.*
Shehab et al. (Fast Dynamic Algorithm for Sequence Alignment based on Bioformatics), vol. 37, No. 7, Jan. 2012.*

(Continued)

*Primary Examiner* — Baoquoc N To
(74) *Attorney, Agent, or Firm* — Alin Corie; Sandy Swain; Micky Minhas

(57) ABSTRACT

Various technologies described herein pertain to parallel local sequence alignment that aligns a query sequence with a database sequence. The database sequence is segmented into a plurality of stripes. A first processing unit can compute Smith-Waterman values for a first stripe of the database sequence across the query sequence based on a cost function that models biological similarity between sequences. Moreover, a second processing unit can compute Smith-Waterman values for a second stripe of the database sequence across the query sequence based on the cost function. Further, a subset of the Smith-Waterman values for the second stripe of the database sequence across the query sequence can be re-computed based on the cost function (e.g., by the first processing unit or the second processing unit). The subset of the Smith-Waterman values to be re-computed can be determined based on a query sequence length and the cost function.

20 Claims, 7 Drawing Sheets

(56) References Cited

OTHER PUBLICATIONS

Lavenier, Dominique, "Fine-Grained Parallel Genomic Sequence Comparison", Retrieved at http://www.intechopen.com/books/parallel-and-distributed-computing/fine-grained-parallel-genomic-sequence-comparison>>, Parallel and Distributed Computing, Alberto Ros (Ed.), Jan. 2010, pp. 273-291.

Shehab, et al., "Fast Dynamic Algorithm for Sequence Alignment based on Bioinformatics", Retrieved at http://research.ijcaonline.org/volume37/number7/px03876636.pdf>>, International Journal of Computer Applications, vol. 37, No. 7, Jan. 2012, pp. 54-61.

Szalkowski, et al., "SWPS3—Fast Multi-Threaded Vectorized Smith-Waterman for IBM Cell/B.E. and ×86/SSE2", Retrieved at <<http://www.biomedcentral.com/content/pdf/1756-0500-1-107.pdf>>, BMC Research Notes, Oct. 29, 2008, pp. 1-4.

Khajeh-Saeed, et al., "Acceleration of the Smith-Waterman Algorithm using Single and Multiple Graphics Processors", Retrieved at <<http://www.nvidia.com/content/cudazone/CUDABrowser/downloads/papers/Acceleration_of_the_SmithWaterman_algorithm_using_single.pdf>>, Journal of Computational Physics, Feb. 20, 2010, pp. 4247-4258.

Schatz, et al., "Fast Exact String Matching on the GPU", Retrieved at <<http://citeseerx.ist.psu.edu/viewdoc/download?doi=10.1.1.94.6278&rep=rep1&type=pdf>>, Center for Bioinformatics and Computational Biology, May 8, 2007, pp. 1-6.

Altschul, et al., "Basic Local Alignment Search Tool", Retrieved at <<http://www.cmu.edu/bio/education/courses/03510/LectureNotes/Altschul1990.pdf>>, Journal of Molecular Biology, vol. 215, Issue.3, Oct. 5, 1990, pp. 403-410.

Li, et al., "Fast and Accurate Long-Read Alignment with Burrows—Wheeler Transform", Retrieved at <<http://bioinformatics.oxfordjournals.org/content/26/5/589.full.pdf+html>>, Oxford Journal of Bioinformatics, vol. 26, Issue.5, Jan. 15, 2010, pp. 589-595.

Ning, et al., "SSAHA: A Fast Search Method for Large DNA Databases", Rerieved at <<http://www.ncbi.nlm.nih.gov/pmc/articles/PMC311141/pdf/X15.pdf>>, Journal of Genome Research, vol. 11, Issue.10, Oct. 2001, pp. 1-6.

Li, et al., "SOAP2: An Improved Ultrafast Tool for Short Read Alignment", Retrieved at <<http://bioinformatics.oxfordjournals.org/content/25/15/1966.full.pdf+html>>, Oxford Journal of Bioinformatics, vol. 25, Issue.15, Jun. 3, 2009, pp. 1966-1967.

Langmead, et al., "Ultrafast and Memory-Efficient Alignment of Short DNA Sequences to the Human Genome", Retrieved at <<http://genomebiology.com/content/pdf/gb-2009-10-3-r25.pdf>>, Genome Biology, vol. 10, Issue 3, Article R25, Mar. 4, 2009, pp. 1-10.

"International Search Report & Written Opinion for PCT Application No. PCT/US2013/075728", Mailed Date: Mar. 31, 2014, Filed Date: Dec. 17, 2013, 10 Pages.

Rognes, et al., "Six-Fold Speed-up of Smith-Waterman Sequence Database Searches Using Parallel Processing on Common Microprocessors", In Bioinformatics, Oxford University Press, vol. 16, Issue 8, Jan. 1, 2000, pp. 699-706.

Farrar, Michael, "Striped Smith-Waterman Speeds Database Searches Six Times over Other SIMD Implementations", In Bioinformatics, vol. 23, Issue 2, Jan. 15, 2007, pp. 156-161.

Steinfadt, et al., "SWAMP: Smith-Waterman using Associative Massive Parallelism", In IEEE International Symposium on Parallel & Distributed Processing, Apr. 14, 2008, pp. 1-8.

Liao, et al., "A Parallel Implementation of the Smith-Waterman Algorithm for Massive Sequences Searching", In 26th Annual International Conference of the IEEE Engineering in Medicine and Biology Society, Sep. 1, 2004, pp. 2817-2820.

\* cited by examiner

PARALLEL LOCAL SEQUENCE ALIGNMENT

BACKGROUND

Proteins and nucleic acids are biological macromolecules that are found in abundance in living organisms, where they function in encoding, transmitting and expressing genetic information. Nucleic acids include DNA (deoxyribonucleic acid) and RNA (ribonucleic acid). For instance, DNA encodes information for building of proteins.

Oftentimes, it is desired to perform local sequence alignment, where similar regions between two nucleotide sequences or protein sequences are identified. Nucleotide or protein sequence alignment can involve solving an approximate string alignment problem for a given cost matrix. Given a database sequence, a query sequence, and a cost function that models biological similarity between sequences, sequence alignment can be performed to find a substring of the database sequence that matches the query sequence.

The Smith-Waterman algorithm is a sequential algorithm based on dynamic programming for performing sequence alignment. The Smith-Waterman algorithm can generate a match, while being inherently sequential. The runtime cost of the Smith-Waterman algorithm can be proportional to the product of a database sequence length and a query sequence length. Thus, the runtime cost can cause the Smith-Waterman algorithm to oftentimes be impractical to implement as the database sequence length increases (e.g., for large genomes). Accordingly, various heuristic based approaches that attempt to find approximate matches have been developed. These conventional heuristic based approaches, however, are commonly less accurate (e.g., miss matches).

SUMMARY

Described herein are various technologies that pertain to parallel local sequence alignment that aligns a query sequence with a database sequence. The database sequence is segmented into a plurality of stripes. A first processing unit can compute Smith-Waterman values for a first stripe of the database sequence across the query sequence based on a cost function that models biological similarity between sequences. Moreover, a second processing unit can compute Smith-Waterman values for a second stripe of the database sequence across the query sequence based on the cost function. Further, a subset of the Smith-Waterman values for the second stripe of the database sequence across the query sequence can be re-computed based on the cost function (e.g., by the first processing unit or the second processing unit). The subset of the Smith-Waterman values to be re-computed can be determined based on a query sequence length and the cost function.

Parallel local sequence alignment as provided herein can parallelize the Smith-Waterman algorithm along the database sequence length, while maintaining the alignment of the sequential Smith-Waterman algorithm. The database sequence is split into a plurality of stripes (e.g., at least the first stripe and the second stripe). Processing units can independently compute Smith-Waterman values for each of the stripes (e.g. in parallel). Thereafter, a subset of the Smith-Waterman values, determined based upon the query sequence length and the cost function, can be re-computed by the processing units (e.g., in parallel). According to various embodiments, the plurality of processing units can be differing processors, differing cores of a multicore processor, differing cores of a multicore graphics processing unit (GPU), comprised in differing computing devices, a combination thereof, or the like.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
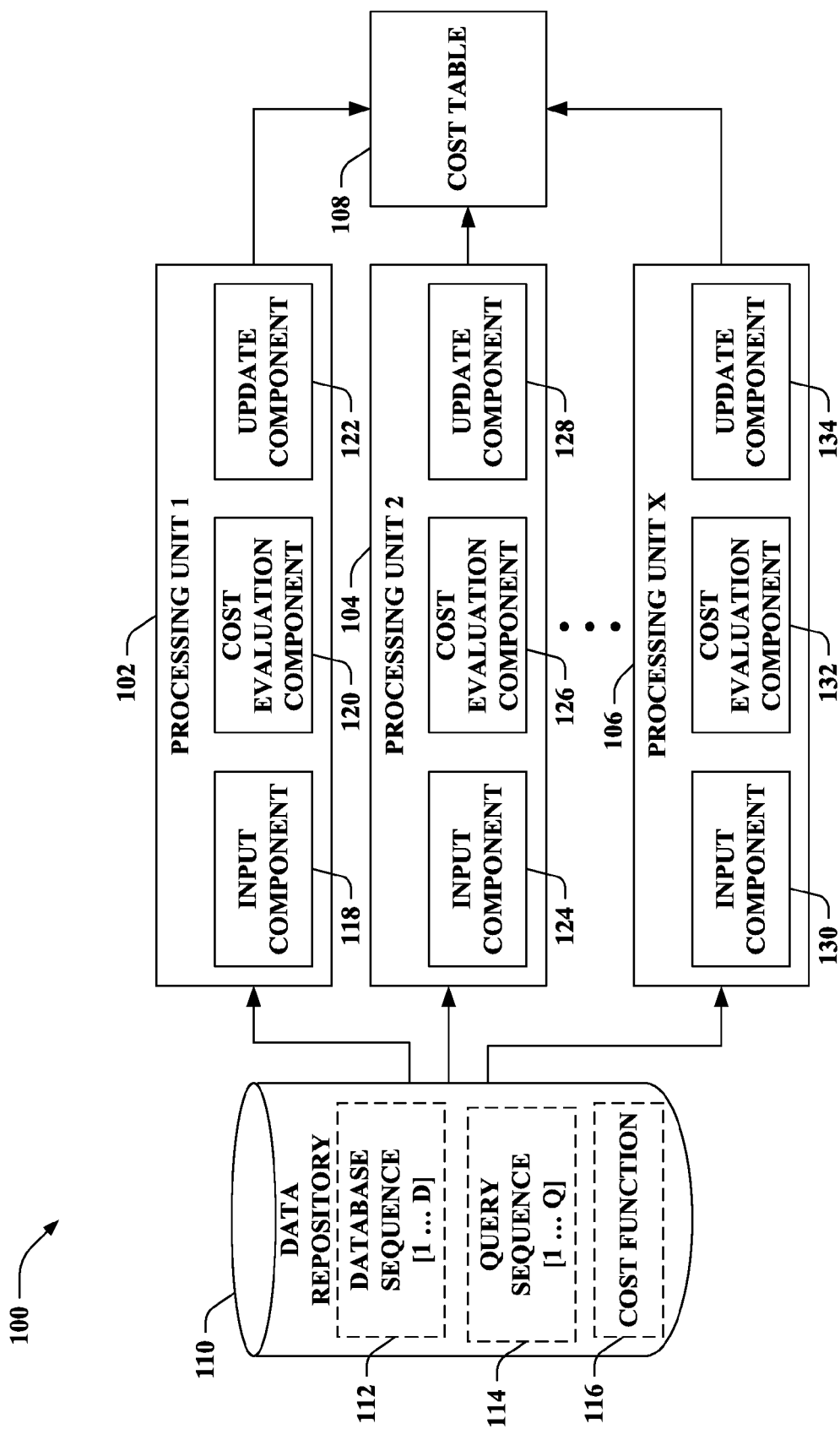
FIG. 1 illustrates a functional block diagram of an exemplary system that performs parallel local sequence alignment.

Various technologies pertaining to local sequence alignment performed in parallel by a plurality of processing units are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

As set forth herein, parallel local sequence alignment between a database sequence and a query sequence can be performed. Parallel local sequence alignment as provided herein can parallelize the Smith-Waterman algorithm along the database sequence length, while maintaining the alignment of the sequential Smith-Waterman algorithm (e.g., mitigating loss of fidelity of matches reported by the algorithm). More particularly, the database sequence can be split into a plurality of stripes. Processing units can independently compute Smith-Waterman values for each of the stripes (e.g. in parallel). Thereafter, a subset of the Smith-Waterman values, determined based upon a query sequence length and a cost function, can be re-computed by the processing units (e.g., in parallel).

Referring now to the drawings, FIG. 1 illustrates a system 100 that performs parallel local sequence alignment. The system 100 includes X processing units: namely, a processing unit 1 102, a processing unit 2 104, ..., and a processing unit X 106 (collectively referred to herein as processing units 102-106), where X can be substantially any integer greater than two. Alternatively, although not shown, it is contemplated that the system 100 can include two processing units (e.g., the processing unit 1 102 and the processing unit 2 104) according to various embodiments. The processing units 102-106 can independently compute Smith-Waterman values included in a cost table 108. As used herein, a Smith-Waterman value refers to a cell score in the cost table 108 generated by employing the Smith-Waterman algorithm.

The system 100 further includes a data repository 110. The data repository 110 can include a database sequence 112 (db) and a query sequence 114 (qr). The database sequence 112 includes a string of D symbols [1 ... D], where D can be substantially any integer. Thus, the database sequence 112 has a database sequence length of D. Moreover, the query sequence 114 includes a string of Q symbols [1 ... Q], where Q can be substantially any integer. Accordingly, the query sequence 114 has a query sequence length of Q.

The database sequence 112 and the query sequence 114 can represent nucleotide sequences or protein sequences. By way of example, the database sequence 112 can represent the human genome, and thus, the database sequence 112 can include billions of symbols (e.g., the database sequence length D can be on the order of billions) that represent DNA base pairs. Following this example, the query sequence 114 can include hundreds or thousands of symbols (e.g., the query sequence length Q can be on the order of hundreds or thousands) that represent DNA base pairs. However, it is to be appreciated that the claimed subject matter is not limited to the foregoing example. Moreover, while many of the examples set forth herein pertain to the database sequence 112 and the query sequence 114 representing nucleotide sequences or protein sequences, in accordance with other examples it is contemplated that the database sequence 112 and the query sequence 114 can represent substantially any other type of data. Thus, the database sequence 112 and the query sequence 114 can represent sequences of musical notes, sequences of text, sequences of documents, or the like. By way of illustration, a query sequence of musical notes can be aligned with a database sequence of musical notes, etc.; however, the claimed subject matter is not so limited.

The data repository 110 can include further include a cost function 116. The cost function 116 models biological similarity between sequences. The cost function 116 can include, for instance, a gap start penalty $G_s$, a gap extend penalty $G_e$, and a cost matrix M. The gap start penalty $G_s$ is a cost to open a new gap between symbols in a sequence (e.g., the database sequence 112 or the query sequence 114). Further, the gap extend penalty $G_e$ is the cost of extending an already opened gap between symbols in a sequence (e.g., the database sequence 112 or the query sequence 114). The gap start penalty $G_s$ is greater than 0. Moreover, the gap extend penalty $G_e$ is greater than 0 and less than or equal to the gap start penalty $G_s$. Moreover, the cost matrix M sets a cost of matching two symbols (e.g., cost of matching adenine to adenine, cost of matching adenine to cytosine, etc.).

The system 100 can perform parallel local sequence alignment to align the query sequence 114 with the database sequence 112. To perform the parallel local sequence alignment, the system 100 can split the database sequence 112 into a plurality of stripes. The plurality of stripes can include at least a first stripe and a second stripe. According to an example, the database sequence 112 can be split into X stripes (e.g., corresponding to the number of processing units 102-106); yet, it is contemplated that the claimed subject matter is not so limited, and instead, the database sequence 112 can be segmented into substantially any other number of stripes.

A stripe is a column-wise partition of a database. In contrast, conventional approaches that attempt to employ wave-front parallelism commonly parallelize along the wave-front, which is an anti-diagonal. Parallelizing along the wave-front oftentimes is employed in conventional approaches because the Smith-Waterman algorithm lacks data dependencies along the anti-diagonal. On the contrary, the techniques set forth herein provide for alleviating an adverse impact due to the column-wise partitions in the database (e.g., the stripes), which break data dependencies column-wise.

According to an example, each of the stripes can have substantially similar lengths. For instance, each stripe can have a stripe length of S (e.g., each stripe can include a string of S symbols from the database sequence 112), where S is an integer less than D. By way of other examples, it is contemplated that two or more of the stripes can have differing lengths.

The stripes cover the database sequence 112. Moreover, due to data dependence associated with the Smith-Waterman algorithm, small overlaps between stripes are employed (e.g., Smith-Waterman values are re-computed within overlap regions of the cost table 108). The overlaps can be determined based upon the cost function 116 used for alignment. Thus, while determined in parallel for the query sequence 114 provided to each of the processing units 102-106, a cell in the cost table 108 having a highest Smith-Waterman value from any of the stripes can be identified as a maximum across stripes.

Further, a traceback can be evaluated from the maximum Smith-Waterman value to produce an alignment between symbols in the query sequence 114 and the symbols in the database sequence 112. Thus, the maximum Smith-Waterman value from the cost table 108 can be detected, and the traceback can be performed from the maximum Smith-Waterman value to produce the alignment between the symbols in the query sequence 114 and the symbols in the database sequence 112.

The processing units 102-106 can each include a plurality of components. More particularly, the processing unit 1 102 can include an input component 118, a cost evaluation component 120, and an update component 122. The input component 118, the cost evaluation component 120, and the update component 122 can be executed by the processing unit 1 102. Similarly, the processing unit 2 104 can include an input component 124, a cost evaluation component 126, and an update component 128, ..., and the processing unit X 106 can include an input component 130, a cost evaluation component 132, and an update component 134. It is to be appreciated that the input components (e.g., the input component 118, the input component 124, ..., and the input component 130) can be substantially similar, the cost evaluation components (e.g., the cost evaluation component 120, the cost evaluation component 126, ..., and the cost evaluation component 132) can be substantially similar, and the update components (e.g., the update component 122, the update component 128, ..., and the update component 134) can be substantially similar.

The following example describes the processing unit 1 102 and the processing unit 2 104. It is to be appreciated, however, that such example can be extended to the remaining processing units 102-106. The input component 118 of the processing unit 1 102 can obtain the query sequence 114 to align with the database sequence 112. The query sequence 114 can similarly be obtained by the input component 124 of the processing unit 2 104.

As noted above, the database sequence 112 is segmented into at least a first stripe and a second stripe. For example, the input component 118 of the processing unit 1 102 can obtain the first stripe of the database sequence 112. The cost evaluation component 120 can utilize the processing unit 1 102 to compute Smith-Waterman values for the first stripe of the database sequence 112 across the query sequence 114 based on the cost function 116 that models biological similarity between sequences. Further following this example, the input component 124 of the processing unit 2 104 can obtain the second stripe of the database sequence 112. The cost evaluation component 120 of the processing unit 2 104 can compute Smith-Waterman values for the second stripe of the database sequence 112 across the query sequence 114. Such computation of the Smith-Waterman values for the first stripe and the second stripe (as well as any other stripe(s) of the database sequence 112 evaluated by the remaining processing units 102-106) can be performed in parallel (e.g., concurrently).

Further, the update component 122 can determine a subset of the Smith-Waterman values for the second stripe of the database sequence 112 across the query sequence 114 to be re-computed. Such determination can be based on the query sequence length Q and the cost function 116. For instance, the update component 122 can determine the subset of the Smith-Waterman values to be re-computed based on the query sequence length Q, the gap start penalty $G_s$, the gap extend penalty $G_e$, and an upper bound of entries in the cost matrix $M_{max}$.

Moreover, the update component 122 can cause the cost evaluation component 120 to re-compute the subset of the Smith-Waterman values for the second stripe of the database sequence 112 across the query sequence 114. Thus, the input component 118 of the processing unit 1 102 can obtain the second stripe of the database sequence 112 (or a portion thereof). The subset of the Smith-Waterman values can be re-computed utilizing the first processing unit 1 102. Such re-computing of the subset of the Smith-Waterman values for the second stripe of the database sequence 112 across the query sequence 114 can be subsequent to computing the Smith-Waterman values for the first stripe of the database sequence 112 across the query sequence 114 (e.g., due to dependence between Smith-Waterman values in the cost table 108 for the Smith-Waterman algorithm). Thus, the re-computation of the subset of the Smith-Waterman values for the second stripe of the database sequence 112 across the query sequence 114 can be based on the Smith-Waterman values for the first stripe of the database sequence 112 across the query sequence 114 computed by the processing unit 1 102.

By way of another example, it is contemplated that the update component 128 of the processing unit 2 104 can alternatively determine the subset of the Smith-Waterman values for the second stripe of the database sequence 112 across the query sequence 114 to be re-computed. Pursuant to this example, the update component 128 of the processing unit 2 104 can cause the cost evaluation component 126 to re-compute the subset of the Smith-Waterman values for the second stripe of the database sequence 112 across the query sequence 114 utilizing the processing unit 2 104. Such re-computation can be based on the Smith-Waterman values for the first stripe of the database sequence 112 across the query sequence 114 computed by the processing unit 1 102 (e.g., obtained from the cost table 108 by the input component 124, etc.).

According to an example, the processing units 102-106 can be differing processors. Following this example, the processing unit 1 102 and the processing unit 2 104 can be different processors. According to another example, the processing units 102-106 can be differing cores of a multicore processor. Thus, the processing unit 1 102 and the processing unit 2 104 can be differing cores of such multicore processor. According to yet another example, the processing units 102-106 can be differing cores of a graphics processing unit (GPU); hence, the processing unit 1 102 and the processing unit 2 104 can be differing cores of the GPU. By way of yet another example, the processing units 102-106 can be comprised in differing computing devices (e.g., differing computing devices within a cluster, etc.). Following this example, the processing unit 1 102 and the processing unit 2 104 can be comprised in differing computing devices. Moreover, it is contemplated that a combination of the foregoing examples can be employed by the system 100.

Figure 2:
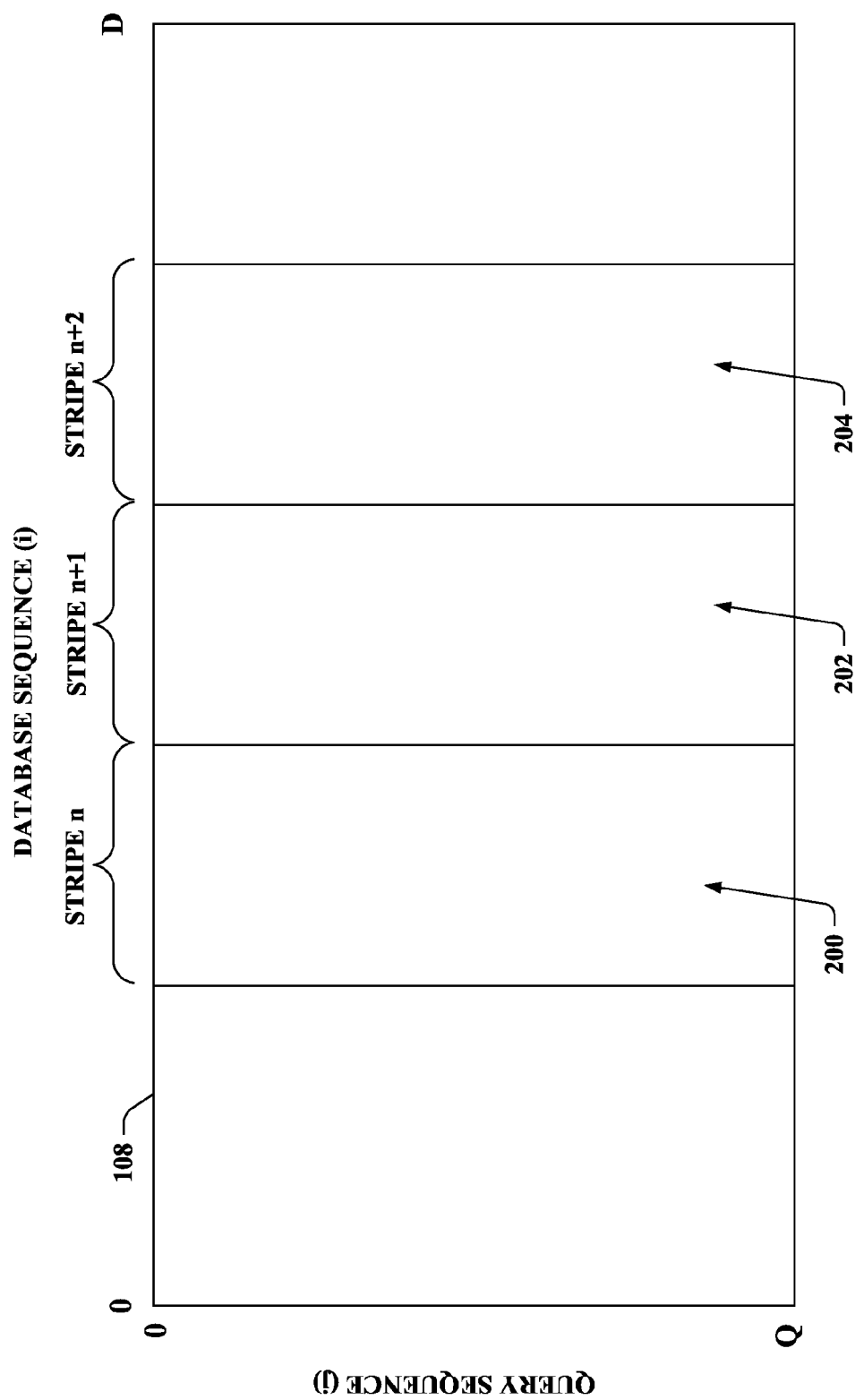
FIG. 2 illustrates an exemplary cost table generated by the system of FIG. 1.

Now turning to FIG. 2, illustrated is the cost table 108 generated by the system 100. The cost table 108 has D+1 columns (e.g., from 0 to D) and Q+1 rows (e.g., from 0 to Q). The processing units 102-106 of FIG. 1 can compute the Smith-Waterman values for the cells of the cost table 108. According to an example, the cost table 108 can be generated by employing the Recurrence function described in the pseudo-code below.

Again, the database sequence is segmented into a plurality of stripes. In the depicted example of FIG. 2 (and similarly FIGS. 3-4), a stripe n, a stripe n+1, and a stripe n+2 are shown. It is to be appreciated, however, that the database sequence can be segmented into substantially any number of stripes, and the claimed subject matter is not limited to the illustrated example.

According to an example, a first processing unit (e.g., the processing unit 1 102 of FIG. 1) can compute Smith-Waterman values for cells in a first portion 200 of the cost table 108, a second processing unit (e.g., the processing unit 2 104 of FIG. 1) can compute Smith-Waterman values for cells in a second portion 202 of the cost table 108, and a third processing unit (e.g., the processing unit X 106 of FIG. 1) can compute Smith-Waterman values for cells in a third portion 204 of the cost table 108. The first portion 200 of the cost table 108 corresponds to the stripe n across the query sequence, the second portion 202 of the cost table 108 corresponds to the stripe n+1 across the query sequence, and the third portion 204 of the cost table 108 corresponds to the stripe n+2 across the query sequence.

The first processing unit can initialize Smith-Waterman values for a first row and a first column of the first portion 200 of the cost table 108. Based upon the initialized values, the first processing unit can compute the Smith-Waterman values for the remainder of the cells in the first portion 200 of the cost table 108. Similarly, the second processing unit can initialize Smith-Waterman values for a first row and a first column of the second portion 202 of the cost table 108, and the third processing unit can initialize Smith-Waterman values for a first row and a first column of the third portion 204 of the cost table 108. Likewise, based upon the initialized values, the second processing unit and the third processing unit can compute the Smith-Waterman values for the respective remainders of the cells in the second portion 202 and the third portion 204 of the cost table 108. Due to the recurrence relation of the Smith-Waterman algorithm, the initialized values can influence a subset of the subsequently computed Smith-Waterman values.

Figure 3:
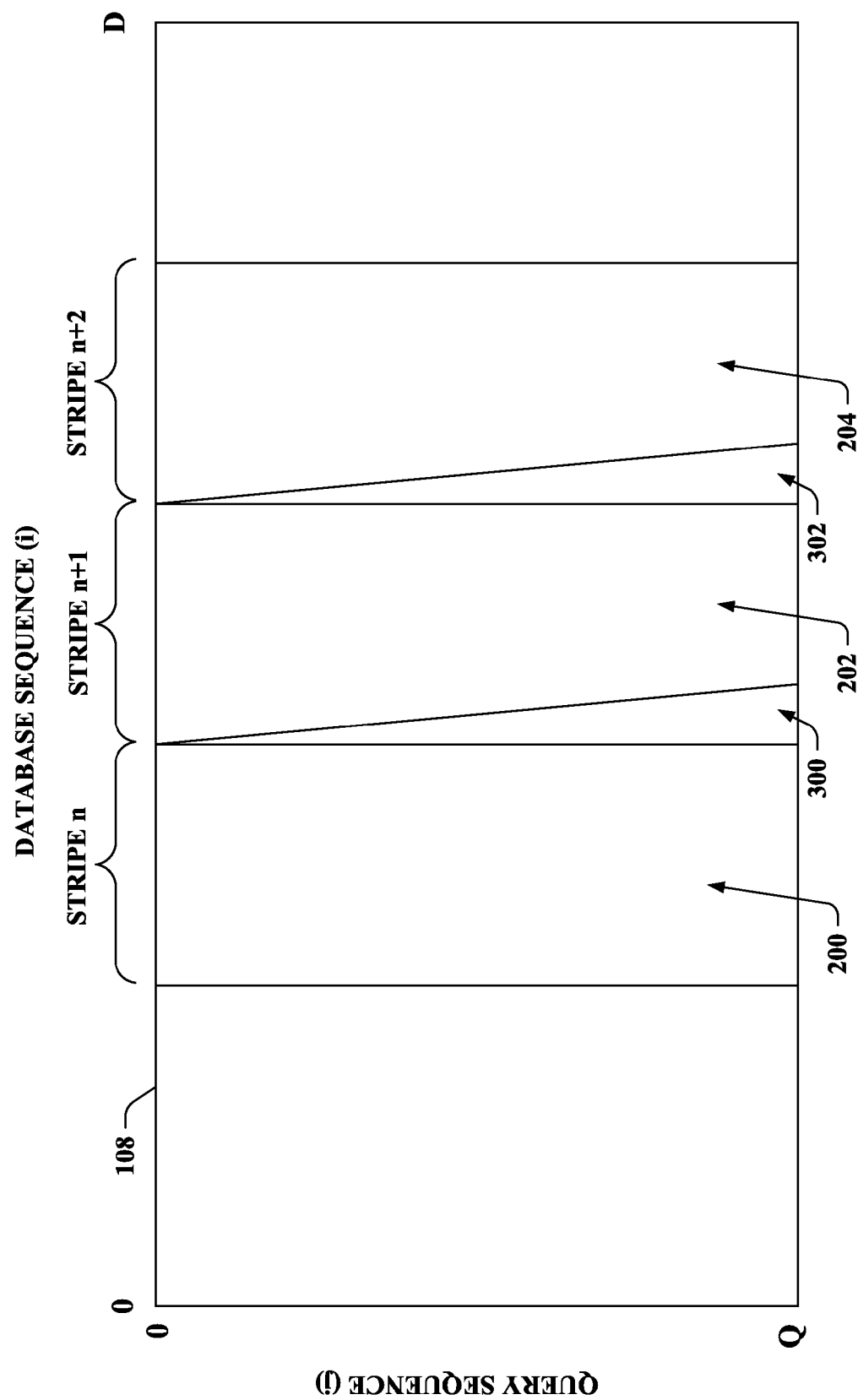
FIGS. 3-4 illustrate various exemplary overlap regions of the cost table of FIG. 2 that include subsets of re-computed Smith-Waterman values.
Figure 4:
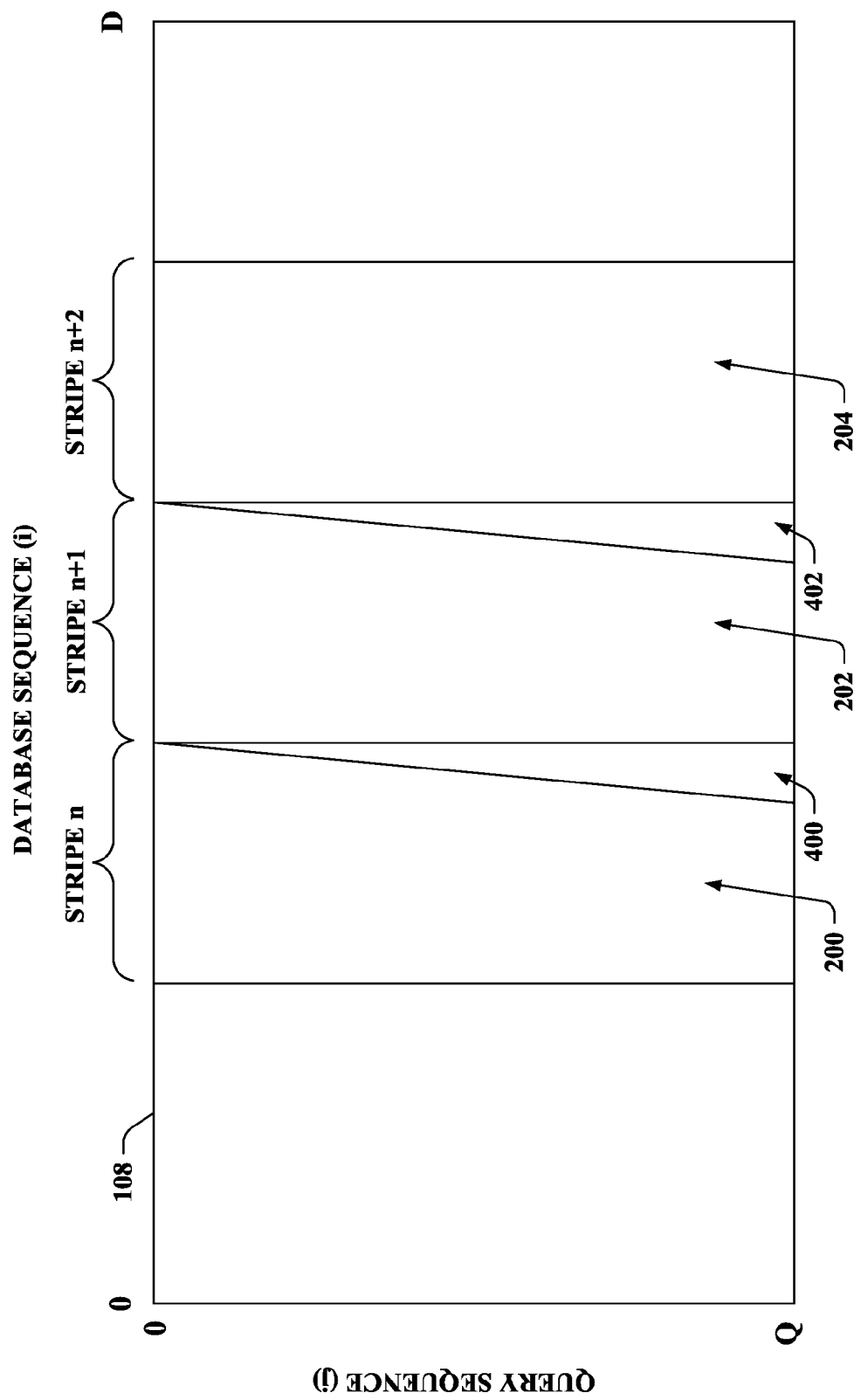

FIGS. 3-4 illustrate various exemplary overlap regions of the cost table 108 (e.g., as shown in FIG. 2) that include subsets of re-computed Smith-Waterman values. It is to be appreciated, however, that other overlap regions are intended to fall within the scope of the hereto appended claims.

With reference to FIG. 3, illustrated is an exemplary depiction of overlap regions of the cost table 108. As depicted, an overlap region 300 is included within the second portion 202 of the cost table 108, and an overlap region 302 is included within the third portion 204 of the cost table 108. The example shown in FIG. 3 corresponds to the pseudo-code for the parallel Smith-Waterman algorithm (ParallelSmithWaterman) set forth below.

Smith-Waterman values included in the overlap region 300 and the overlap region 302 are re-computed. Thus, the Smith-Waterman values included in the overlap region 300 (e.g., a subset of the Smith-Waterman values for the stripe n+1 across the query sequence) can be re-computed based upon Smith-Waterman values from the first portion 200 of the cost table 108, and the Smith-Waterman values included in the overlap region 302 (e.g., a subset of the Smith-Waterman values for the stripe n+2 across the query sequence) can be re-computed based upon Smith-Waterman values from the second portion 202 of the cost table 108.

Turning to FIG. 4, illustrated is another exemplary depiction of overlap regions of the cost table 108. As depicted, an overlap region 400 is included within the first portion 200 of the cost table 108, and an overlap region 402 is included within the second portion 202 of the cost table 108.

Smith-Waterman values included in the overlap region 400 and the overlap region 402 are re-computed. Thus, the Smith-Waterman values included in the overlap region 400 (e.g., a subset of the Smith-Waterman values for the stripe n across the query sequence) can be re-computed based upon Smith-Waterman values from the second portion 202 of the cost table 108, and the Smith-Waterman values included in the overlap region 402 (e.g., a subset of the Smith-Waterman values for the stripe n+1 across the query sequence) can be re-computed based upon Smith-Waterman values from the third portion 204 of the cost table 108.

Again, reference is made to FIG. 1. The Smith-Waterman algorithm described herein can perform local sequence alignment. Accordingly, the Smith-Waterman algorithm can attempt to find local regions of similarity or sub-sequence homology, aligning highly conserved regions between the database sequence 112 and the query sequence 114. Since such local alignment need not stretch across the entire length of the strings, a local alignment can begin and end substantially anywhere within the database sequence 112 and the query sequence 114. The Smith-Waterman algorithm is a dynamic programming algorithm that performs local sequence alignment on two strings of symbols, namely, the database sequence 112 and the query sequence 114. The length of the database sequence 112 is D and the length of the query sequence 114 is Q.

A dynamic programming approach that uses tables or matrices to preserve values and mitigate recalculation can be utilized in connection with the Smith-Waterman algorithm. This can create data dependencies among different Smith-Waterman values. For instance, a Smith-Waterman value for an entry (i, j) of the cost table 108 can be computed based on prior computation of entries (i−1, j−1), (i, j−1), and (i−1, j) of the cost table 108. A recursive relationship between the computations is described in further detail below.

The Smith-Waterman algorithm allows for insertion and deletion of symbols in the database sequence 112 and the query sequence 114. However, such evaluation can be computationally and memory intensive.

The following pseudo-code shows the sequential implementation of the Smith-Waterman algorithm with the cost matrix M that sets the cost of matching two symbols, the gap start penalty $G_s$, and the gap extend penalty $G_e$.

```
// Parameters
// cost matrix M_min <= M[i,j[ <= M_max
Cost M[Sym, Sym];
// gap start, 0 < G_s
Cost G_s;
// gap extend, 0 < G_e <= G_s
Cost G_e;
// Input
Sym db [1...D]; // database sequence
Sym qr [1...Q]; //query sequence
// Cost tables
Cost bc [0...D, 0...Q]; // best cost
Cost ig [0...D, 0...Q]; // gap at i
Cost jg [0...D, 0...Q]; // gap at j
Init ( ) {
    bc[0,0] = 0;
    for i in (1...D)
        bc[i,0] = jg[i,0] = 0;
        ig[i,0] = −G_s − i*G_e;
    for j in (1...Q)
        bc[0, j] = ig[0,j] = 0;
        jg[0, j] = −G_s − j*G_e;
}
Recurrence (i,j) {
    ig[i,j] = max ( ig[i−1, j]−G_e,
                   bc[i−1,j]−G_s−G_e );
    jg[i, j] = max( jg[i, j−1] − G_e,
                   bc[i,j−1]−G_s−G_e);
    bc[i,j] = max( 0,
                   bc[i−1, j−1] + M(db[i], qr[i]),
                   ig[i,j] ,
                   jg[i,j] );
}
SmithWaterman( ) {
    Init ( );
    for i in (1...D)
        for j in (1...Q)
            Recurrence (i,j);
}
```

As set forth above, the Smith-Waterman algorithm can compute three cost tables: a best cost table (bc), a gap at i table (ig), and a gap at j table (jg). The cost table 108 can be the best cost table (bc), the gap at i table (ig), or the gap at j table (jg). The Init function initializes the tables. A column and a row of the each of the tables are initialized by the Init function. Moreover, the Recurrence function is called in a particular order (e.g., by the for loops in the SmithWaterman function) to fill in remainders of the tables.

The algorithm as presented above includes a loop carried dependence where (i, j) entries of the cost tables depend on (i−1, j−1), (i, j−1), and (i−1, j). Conventionally, it has been observed that elements of an anti-diagonal depend on values on smaller anti-diagonals; thus, many conventional approaches attempt to employ wave-front parallelism. In contrast, the approach set forth herein provides parallelism in stripes.

An entry (i, j) influences another entry (i', j') if there is data dependence from bc[i, j] to bc[i', j']. Syntactically from the recurrence, (i, j) influences (i', j') only when i≤i' and j≤j'. Yet, the entry (i, j) can influence a smaller number of entries as compared to the syntactic constraint.

More particularly, the entry (i, j) can have a horizontal influence and a vertical influence. For the horizontal influence, the entry (i, j) influences (i', j') only if bc[i, j]≥$G_s$+(i'−i)*$G_e$. Further, for the vertical influence, the entry (i, j) influences (i', j') only if bc[i, j]≥$G_s$+(j'−j)*$G_e$.

Based on the horizontal and vertical influences set forth above, it follows that the entry (i, j) can influence (i', j') only if bc[i, j]≥$G_s$+g*$G_e$−d*$M_{max}$, where g=|(i'−i)−(j'−j)|, d=min (i'−i, j'−j), and $M_{max}$ is an upper bound of the entries in M. Further, it follows that bc[i, j]≤min(i, j)*$M_{max}$. Accordingly, it can be shown that the entry (i, j) cannot influence (i', j') if i'−i≤(j'*$M_{max}$−$G_s$)/$G_e$. The foregoing can be utilized by the update component 122 (and similarly the update component 128, . . . , and the update component 134) to determine the subset of the Smith-Waterman values to re-compute.

Accordingly, the processing units 102-106 can independently compute alignment of the query sequence on different parts of the database sequence 112 by determining the overlap region(s), where Smith-Waterman values are re-computed within the overlap region(s). This can be represented by the following pseudo-code:

```
ParallelSmithWaterman(StripeLenS) {
    Init ( );
    parallel for s in (0...D/S)
        for i in (1...S)
            for j in (1...Q)
                Recurrence(s*S+i, j);
    parallel for s in (1...D/S)
        for i in (1...(Q*M_max−G_s)/G_e)
            for j in (1...Q)
                if i <= (j*M_max−G_s)/G_e
                    Recurrence (s*S+i,j);
}
```

Accordingly, the three cost functions can be initialized by the Init function. Moreover, the Recurrence function is called by the processing units 102-106 in parallel (e.g., the cost evaluation component 120, the cost evaluation component 126, . . . , and the cost evaluation component 132) to compute the Smith-Waterman values respectively for each of the stripes across the query sequence 114 (e.g., as shown in FIG. 2). Thereafter, subsets of the Smith-Waterman values (e.g., entries in the cost table 108) for stripes other than the first stripe to be re-computed can be determined (e.g., by the update component 122, the update component 128, . . . , and the update component 134). Such determination can respectively be made by evaluating whether i≤(j*$M_{max}$−Gs)/Ge. The foregoing determination can be analyzed for i from 1 to (Q*$M_{max}$−$G_s$)/$G_e$ and for j from 1 to Q. Moreover, such subsets of the Smith-Waterman values can thereafter be re-computed (e.g., as shown in FIG. 3) by calling the Recurrence function (e.g., by the cost evaluation component 120, the cost evaluation component 126, . . . , and the cost evaluation component 132). The re-computation of the subset of the Smith-Waterman values can be performed in parallel.

By way of another example, it is contemplated that the example set forth above can provide a bound on the re-computation. Thus, whether i≤(j*$M_{max}$−Gs)/Ge for i from 1 to (Q*$M_{max}$−$G_s$/$G_e$ and for j from 1 to Q can be evaluated to provide a lower bound when determining the subset of the Smith-Waterman values to be re-computed.

Figure 5:
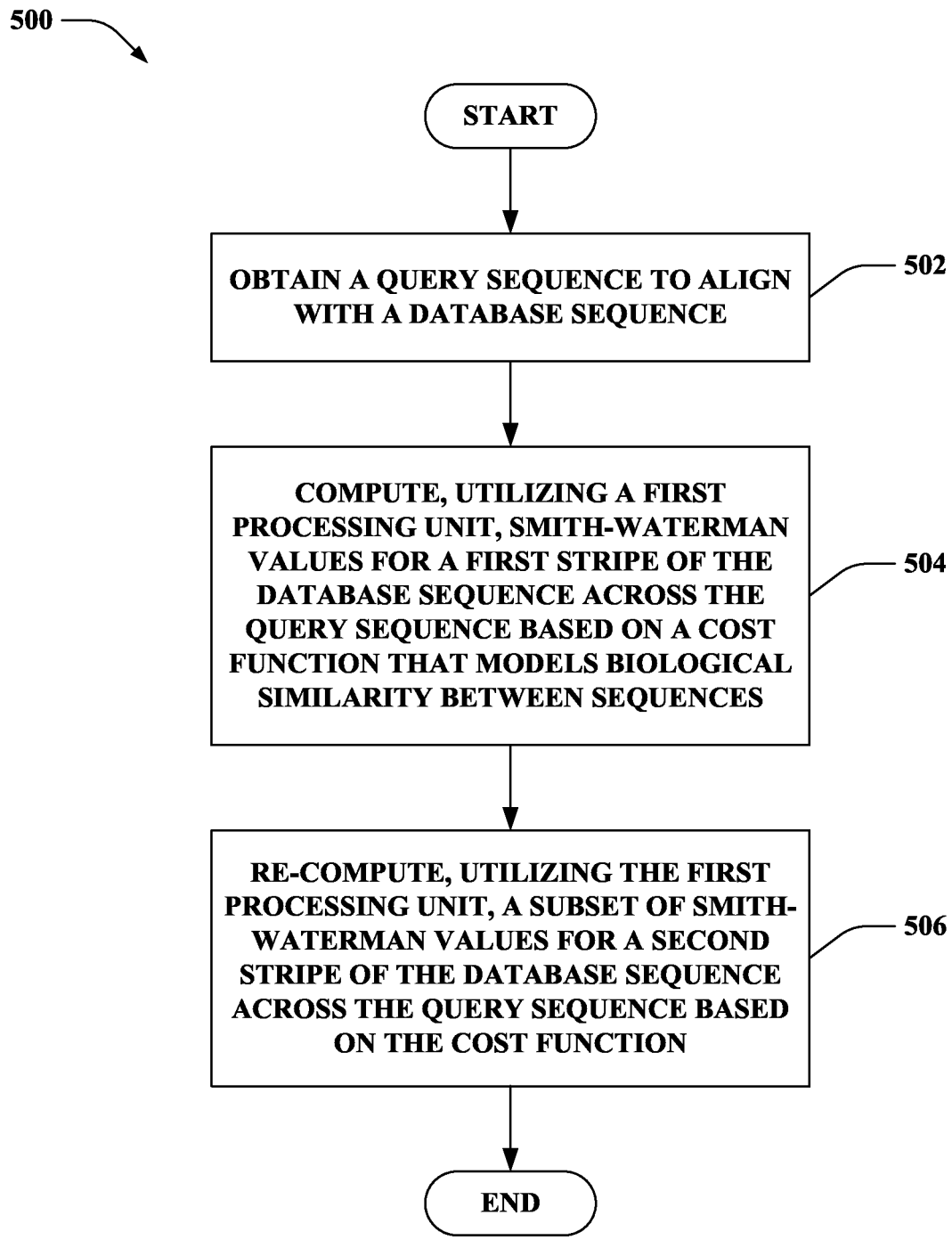
FIG. 5 is a flow diagram that illustrates an exemplary methodology configured for execution by a first processing unit.
Figure 6:
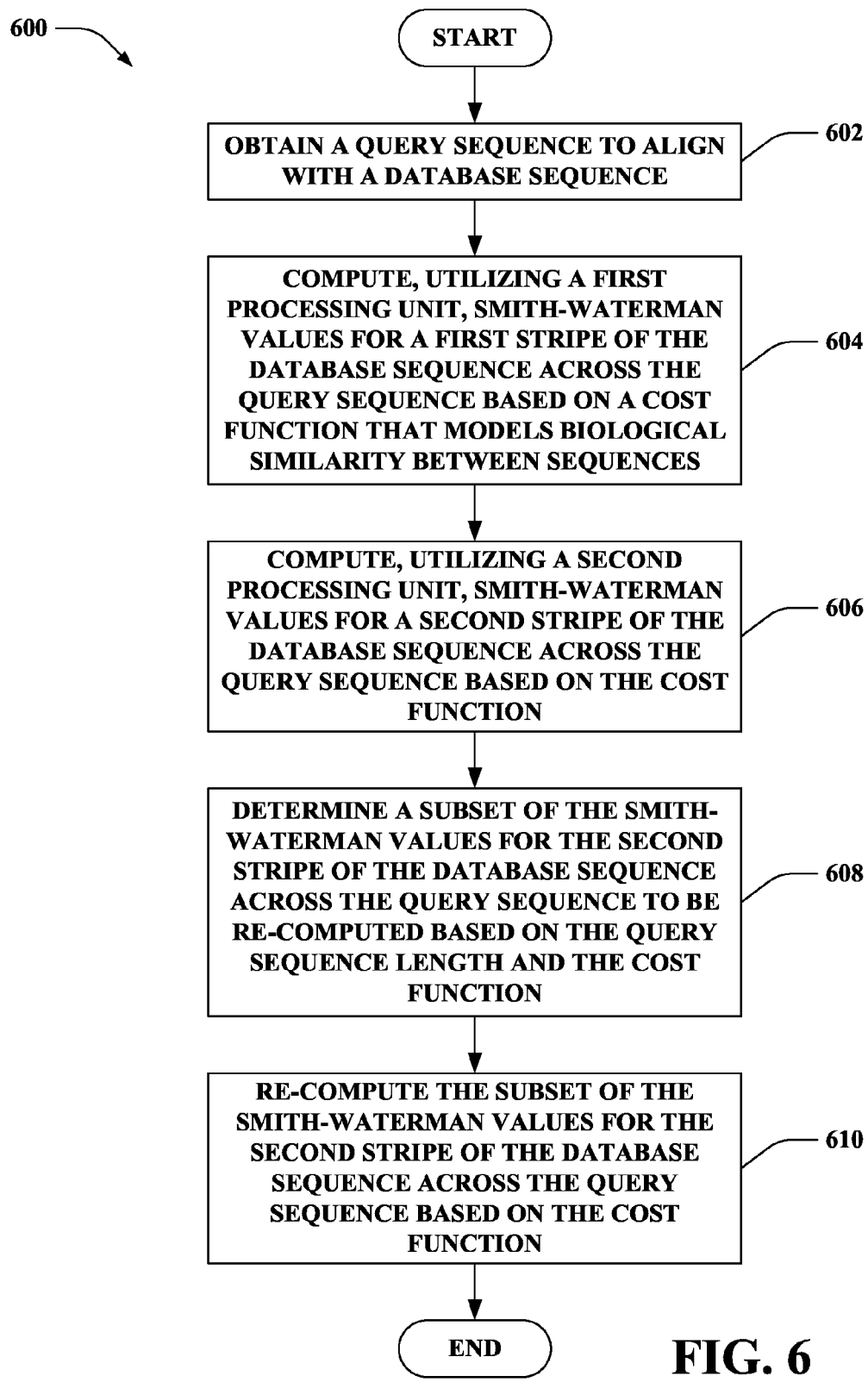
FIG. 6 is a flow diagram that illustrates an exemplary methodology configured for execution by a plurality of processing units of a computing device.

FIGS. 5-6 illustrate exemplary methodologies relating to parallel local sequence alignment. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

FIG. 5 illustrates a methodology 500 configured for execution by a first processing unit. At 502, a query sequence to align with a database sequence can be obtained. The query sequence can include a string of symbols having a query sequence length. Moreover, the database sequence can include a string of symbols having a database sequence length. The database sequence can be segmented into at least a first stripe and a second stripe.

At 504, Smith-Waterman values for the first stripe of the database sequence across the query sequence can be computed based on a cost function that models biological similarity between sequences. Such computation can be performed utilizing the first processing unit. Moreover, Smith-Waterman values for the second stripe of the database sequence across the query sequence can be computed utilizing a second processing unit. The first processing unit and the second processing unit can concurrently compute the respective Smith-Waterman values.

At 506, a subset of the Smith-Waterman values for the second stripe of the database sequence across the query sequence can be re-computed based on the cost function. The subset of the Smith-Waterman values to be re-computed can be determined based on the query sequence length and the cost function. Such re-computation can be performed utilizing the first processing unit, for example. According to another example, such re-computation can be performed utilizing the second processing unit. Yet, the claimed subject matter is not limited to the foregoing examples.

Now turning to FIG. 6, illustrated is a methodology 600 configured for execution by a plurality of processing units of a computing device. At 602, a query sequence to align with a database sequence can be obtained. Similar to above, the query sequence can include a string of symbols having a query sequence length. Further, the database sequence can include a string of symbols having a database sequence length. The database sequence can be split into at least a first stripe and a second stripe.

At 604, Smith-Waterman values for the first stripe of the database sequence across the query sequence can be computed based on a cost function that models biological similarity between sequences. The computation of the Smith-Waterman values for the first stripe can be performed utilizing a first processing unit from the plurality of processing units. At 606, Smith-Waterman values for a second stripe of the database sequence across the query sequence can be computed based on the cost function. The computation of the Smith-Waterman values for the second stripe can be performed utilizing a second processing unit from the plurality of processing units. By way of example, the first processing unit and the second processing unit can concurrently compute the Smith-Waterman values.

At 608, a subset of the Smith-Waterman values for the second stripe of the database sequence across the query sequence to be re-computed can be determined based on the query sequence length and the cost function. At 610, the subset of the Smith-Waterman values for the second stripe of the database sequence across the query sequence can be re-computed based on the cost function. It is contemplated that the subset of the Smith-Waterman values can be re-computed by the first processing unit. According to another example, it is contemplated that the subset of the Smith-Waterman values can be re-computed by the second processing unit.

In accordance with an example, it is contemplated that Smith-Waterman values for a third stripe of the database sequence across the query sequence can be computed based on the cost function, where such computation can be performed utilizing a third processing unit from the plurality of processing units. Moreover, a second subset of the Smith-Waterman values for the third stripe of the database sequence across the query sequence to be re-computed can be determined based on the query sequence length and the cost function. Further, the second subset of the Smith-Waterman values for the third stripe of the database sequence across the query sequence can be re-computed. Following the foregoing example, the subset of the Smith-Waterman values and the second subset of the Smith-Waterman values can be concurrently re-computed utilizing differing processing units from the plurality of processing units. It is to be appreciated, however, that the claimed subject matter is not limited to the foregoing example.

Figure 7:
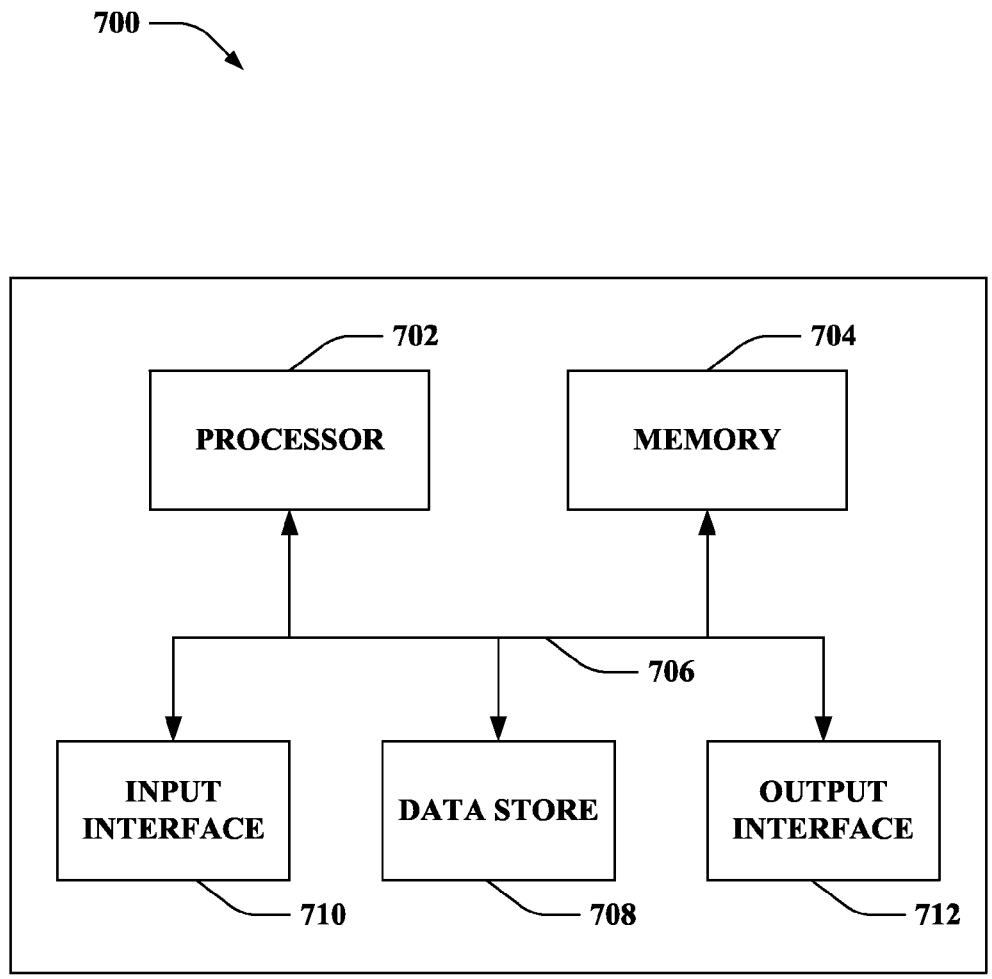
FIG. 7 illustrates an exemplary computing device.

Referring now to FIG. 7, a high-level illustration of an exemplary computing device 700 that can be used in accordance with the systems and methodologies disclosed herein is illustrated. For instance, the computing device 700 may be used in a system that performs parallel local sequence alignment. The computing device 700 includes at least one processor 702 that executes instructions that are stored in a memory 704. The at least one processor 702 can be and/or include one or more of the processing units 102-106. The instructions may be, for instance, instructions for implementing functionality described as being carried out by one or more components discussed above or instructions for implementing one or more of the methods described above. The processor 702 may access the memory 704 by way of a system bus 706. In addition to storing executable instructions, the memory 704 may also store a database sequence (or a portion thereof), a query sequence, a cost function, a cost table, and so forth.

The computing device 700 additionally includes a data store 708 that is accessible by the processor 702 by way of the system bus 706. The data store 708 may include executable instructions, a database sequence (or a portion thereof), a query sequence, a cost function, a cost table, etc. The computing device 700 also includes an input interface 710 that allows external devices to communicate with the computing device 700. For instance, the input interface 710 may be used to receive instructions from an external computer device, from a user, etc. The computing device 700 also includes an output interface 712 that interfaces the computing device 700 with one or more external devices. For example, the computing device 700 may display text, images, etc. by way of the output interface 712.

It is contemplated that the external devices that communicate with the computing device 700 via the input interface 710 and the output interface 712 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 700 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 700 may be a distributed system. Thus, for instance, several devices may be in communication by way of a network connection and may collectively perform tasks described as being performed by the computing device 700.

As used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices.

Further, as used herein, the term "exemplary" is intended to mean "serving as an illustration or example of something."

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. A method of aligning a query sequence with a database sequence, the query sequence comprises a string of symbols having a query sequence length, the database sequence comprises a string of symbols having a database sequence length, and the database sequence being segmented into at least a first stripe and a second stripe, the method comprising:
   computing, utilizing a first processing unit, Smith-Waterman values for cells in a first column-wise partition of a table based on a cost function that models similarity between sequences, the first column-wise partition corresponding to the first stripe of the database sequence across the query sequence, wherein Smith-Waterman values for cells in a second column-wise partition of the table are computed utilizing a second processing unit, the second column-wise partition corresponding to the second stripe of the database sequence across the query sequence;
   re-computing a subset of the Smith-Waterman values for the cells in the second column-wise partition of the table based on the cost function, the subset of the Smith-Waterman values being based on the query sequence length and the cost function; and
   producing an alignment between the symbols in the query sequence and the symbols in the database sequence based on Smith-Waterman values for cells of the table, the Smith-Waterman values for the cells of the table comprise at least the Smith-Waterman values for the cells in the first column-wise partition and the Smith-Waterman values for the cells in the second column-wise partition.

2. The method of claim 1, wherein the cost function comprises a gap start penalty, a gap extend penalty, and a cost matrix that sets a cost of matching two symbols.

3. The method of claim 2, further comprising determining the subset of the Smith-Waterman values to be re-computed based on the query sequence length, the gap start penalty, the gap extend penalty, and an upper bound of entries in the cost matrix.

4. The method of claim 1, further comprising performing a traceback from a maximum Smith-Waterman value in the table to produce the alignment between the symbols in the query sequence and the symbols in the database sequence.

5. The method of claim 1, wherein:
   the first processing unit and the second processing unit concurrently compute the Smith-Waterman values for the cells in the first column-wise partition of the table and the Smith-Waterman values for the cells in the second column-wise partition of the table; and
   the subset of the Smith-Waterman values for the cells in the second column-wise partition of the table are re-computed subsequent to the concurrent computation of the Smith-Waterman values for the cells in the first column-wise partition of the table and the Smith-Waterman values for the cells in the second column-wise partition of the table.

6. The method of claim 1, wherein the first processing unit and the second processing unit are differing processors.

7. The method of claim 1, wherein the first processing unit and the second processing unit are differing cores of a multicore processor.

8. The method of claim 1, wherein the first processing unit and the second processing unit are differing cores of a graphics processing unit (GPU).

9. The method of claim 1, wherein the first processing unit and the second processing unit are comprised in differing computing devices.

10. The method of claim 1, wherein the query sequence and the database sequence represent sequences of biological macromolecules.

11. The method of claim 1, wherein the query sequence and the database sequence represent sequences of musical notes.

12. A method of aligning a query sequence with a database sequence, the query sequence comprises a string of symbols having a query sequence length, the database sequence comprises a string of symbols having a database sequence length, and the database sequence being segmented into at least a first stripe and a second stripe, the method comprising:
   at a first processing unit:
      computing, utilizing the first processing unit, Smith-Waterman values for cells in a first column-wise partition of a table based on a cost function that models similarity between sequences, the first column-wise partition corresponding to the first stripe of the database sequence across the query sequence;
   at a second processing unit, the second processing unit differing from the first processing unit:
      computing, utilizing the second processing unit, Smith-Waterman values for cells in a second column-wise partition of the table based on the cost function, the second column-wise partition corresponding to the second stripe of the database sequence across the query sequence;
   at one of the first processing unit or the second processing unit:
      determining a subset of the Smith-Waterman values for the cells in the second column-wise partition of the table to re-compute based on the query sequence length and the cost function; and
      re-computing the subset of the Smith-Waterman values for the cells in the second column-wise partition of the table based on the cost function; and
   producing an alignment between the symbols in the query sequence and the symbols in the database sequence based on Smith-Waterman values for cells of the table, the Smith-Waterman values for the cells of the table comprise at least the Smith-Waterman values for the cells in the first column-wise partition and the Smith-Waterman values for the cells in the second column-wise partition.

13. The method of claim 12, wherein the first processing unit and the second processing unit concurrently compute the Smith-Waterman values.

14. The method of claim 12, wherein the database sequence is further segmented into a third stripe, the method further comprising:
   at a third processing unit, the third processing unit differing from the first processing unit and the second processing unit:
      computing, utilizing the third processing unit, Smith-Waterman values for cells in a third column-wise partition of the table based on the cost function, the third column-wise partition corresponding to the third stripe of the database sequence across the query sequence;

at one of the first processing unit, the second processing unit, or the third processing unit:
determining a subset of the Smith-Waterman values for the cells in the third column-wise partition of the table to re-compute based on the query sequence length and the cost function; and
re-computing the subset of the Smith-Waterman values for the cells in the third column-wise partition of the table based on the cost function;
wherein the Smith-Waterman values for the cells of the table further comprise the Smith-Waterman values for the cells in the third column-wise partition.

15. The method of claim 14, wherein the subset of the Smith-Waterman values for the cells in the second column-wise partition of the table and the subset of the Smith-Waterman values for the cells in the third column-wise partition of the table are concurrently re-computed utilizing differing processing units.

16. The method of claim 12, wherein the cost function comprises a gap start penalty, a gap extend penalty, and a cost matrix that sets a cost of matching two symbols, and wherein the subset of the Smith-Waterman values for the cells in the second column-wise partition of the table to re-compute are determined based on the query sequence length, the gap start penalty, the gap extend penalty, and an upper bound of entries in the cost matrix.

17. The method of claim 12, wherein the first processing unit and the second processing unit comprise one or more of differing processors, differing cores of a multicore processor, or differing cores of a graphics processing unit (GPU).

18. The method of claim 12, producing the alignment between the symbols in the query sequence and the symbols in the database sequence based on the Smith-Waterman values for the cells of the table further comprising:
detecting a maximum Smith-Waterman value from the Smith-Waterman values for the cells of the table; and
performing a traceback from the maximum Smith-Waterman value to produce the alignment between the symbols in the query sequence and the symbols in the database sequence.

19. A computing device, comprising:
a processing unit; and
a memory that comprises computer-executable instructions that, when executed by the processing unit, cause the processing unit to perform acts including:
computing, utilizing the processing unit, Smith-Waterman values for cells in a first column-wise partition of a table based on a cost function that models similarity between sequences, the first column-wise partition of the table corresponding to a first stripe of a database sequence across the query sequence, the query sequence comprises a string of symbols, the database sequence comprising a string of symbols, the data base sequence being segmented into at least the first stripe and a second stripe, wherein Smith-Waterman values for cells in a second column-wise partition of the table are computed in parallel utilizing a second processing unit, the second column-wise partition corresponding to the second stripe of the database sequence across the query sequence;
determining a subset of the Smith-Waterman values for the cells in the second column-wise partition of the table to re-compute based on a length of the string of the symbols of the query sequence and the cost function;
re-computing, utilizing the first processing unit, the subset of the Smith-Waterman values for the cells in the second column-wise partition of the table based on the cost function; and
producing an alignment between the symbols in the query sequence and the symbols in the database sequence based on Smith-Waterman values for cells of the table, the Smith-Waterman values for the cells of the table comprise at least the Smith-Waterman values for the cells in the first column-wise partition and the Smith-Waterman values for the cells in the second column-wise partition.

20. The computing device of claim 19, further comprising the second processing unit.

* * * * *